United States Patent
Guger et al.

(10) Patent No.: US 11,207,491 B2
(45) Date of Patent: Dec. 28, 2021

(54) DEVICE AND METHOD FOR THE LEARNING OF THE DELIBERATE CONTROL OF A SPECIFIED BODY PART BY A TEST SUBJECT

(71) Applicants: Christoph Guger, Piberbach (AT); Guenter Edlinger, Graz (AT)

(72) Inventors: Christoph Guger, Piberbach (AT); Guenter Edlinger, Graz (AT)

(*) Notice: Subject to any disclaimer, the term of this patent is extended or adjusted under 35 U.S.C. 154(b) by 287 days.

(21) Appl. No.: 16/346,381

(22) PCT Filed: May 14, 2018

(86) PCT No.: PCT/AT2018/060095
§ 371 (c)(1),
(2) Date: Apr. 30, 2019

(87) PCT Pub. No.: WO2019/051515
PCT Pub. Date: Mar. 21, 2019

(65) Prior Publication Data
US 2020/0061333 A1    Feb. 27, 2020

(30) Foreign Application Priority Data
Sep. 15, 2017   (AT) .............................. A 50775/2017

(51) Int. Cl.
*A61M 21/02*   (2006.01)
*A61B 5/0482*   (2006.01)
(Continued)

(52) U.S. Cl.
CPC ............. *A61M 21/02* (2013.01); *A61B 5/375* (2021.01); *A61B 5/38* (2021.01); *A61B 5/483* (2013.01);
(Continued)

(58) Field of Classification Search
CPC ... A61N 1/0472; A61N 1/0456; A61M 21/02; A61M 2021/0022; A61M 2021/0066;
(Continued)

(56) References Cited

U.S. PATENT DOCUMENTS 9,357,938 B2    6/2016    Ang et al.
9,538,934 B2    1/2017    Ang et al.
(Continued)

FOREIGN PATENT DOCUMENTS

| WO | 2011123059 A1 | 10/2011 |
| WO | 2011123072 A1 | 10/2011 |
| WO | 2016033686 A1 | 3/2016 |

OTHER PUBLICATIONS

Pfurtscheller, G., et al., "Rehabilitation with Brain-Computer Interface Systems", Computer IEEE Computer Society, USA, Oct. 10, 2008, pp. 58-65; ISSN: 0018-9162, XP011292791.

*Primary Examiner* — Christine H Matthews
*Assistant Examiner* — Joshua Daryl D Lannu
(74) *Attorney, Agent, or Firm* — Laurence A. Greenberg; Werner H. Sterner; Ralph E. Locher

(57) ABSTRACT

A training and simulation assembly for the learning of deliberate control of a specified body part by a test subject contains an electrode cap, which has a number of electrodes, and an evaluation unit, which is configured to measure voltages present at the electrodes and to provide measurement results as EEG measurement data. The evaluation unit analyzes the EEG measurement data for the presence of a mental act and to determine a correspondence value, which indicates the correspondence of the EEG measurement data with reference values defined by the mental act. A control unit and a simulation unit are provided. The simulation unit stimulates the body of the test subject at a specified point of the body and/or to trigger a motion. The control unit controls
(Continued)

the stimulation unit and the ability to apply an indicating stimulus to the body part by the stimulation unit.

13 Claims, 1 Drawing Sheet

(51) Int. Cl.
    *A61B 5/00*     (2006.01)
    *A61N 1/04*     (2006.01)
    *A61B 5/0484*     (2006.01)
    *A61B 5/38*     (2021.01)
    *A61B 5/375*     (2021.01)
    *A61M 21/00*     (2006.01)

(52) U.S. Cl.
    CPC .......... *A61B 5/4851* (2013.01); *A61B 5/6803* (2013.01); *A61B 5/7415* (2013.01); *A61B 5/7455* (2013.01); *A61N 1/0456* (2013.01); *A61N 1/0472* (2013.01); *A61M 2021/0022* (2013.01); *A61M 2021/0027* (2013.01); *A61M 2021/0066* (2013.01); *A61M 2021/0072* (2013.01)

(58) Field of Classification Search
    CPC .. A61M 2021/0027; A61M 2021/0072; A61B 5/483; A61B 5/486; A61B 5/6803; A61B 5/375; A61B 5/38; A61B 5/7455; A61B 5/369; A61B 5/4851; A61B 5/7415
    See application file for complete search history.

(56) References Cited

U.S. PATENT DOCUMENTS

| | | |
|---|---|---|
| 10,194,858 B2 | 2/2019 | Chin et al. |
| 2013/0138011 A1* | 5/2013 | Ang ........................ A61B 5/374 |
| | | 600/545 |
| 2017/0181915 A1* | 6/2017 | Ang ........................ A61B 5/1126 |
| 2018/0239430 A1* | 8/2018 | Tadi ........................ H01L 33/58 |

* cited by examiner

DEVICE AND METHOD FOR THE LEARNING OF THE DELIBERATE CONTROL OF A SPECIFIED BODY PART BY A TEST SUBJECT

BACKGROUND OF THE INVENTION

Field of the Invention

From the prior art, different measuring methods and devices are known for the detection of different mental activities of a person and for controlling actions that depend on mental activities. The prior art also contains individual, so-called brain-computer interfaces which are used to determine, further process and visualize the processes running inside the brain of a person in a variety of ways.

Such interfaces are of considerable importance in examining test subjects in the late stage of neurological diseases or subjects with disturbances of consciousness or cognitive impairments, for whom no other means of communication, such as speech, signing, etc. are available, as to how strong their individual subjective perceptual capacity is at a given time.

In addition, different measurement techniques are known from the prior art for determining the perceptual capacity or perception quality of test subjects. In such known methods, different types of stimuli are applied to the test subject. Based on the response of the test subject in the form of brain currents, it is tested whether or not the test subject concerned shows an adequate level of mental activity due to the stimuli.

The learning outcomes necessarily acquired by the test subject during the detection of different mental activities or the quantification of the perceptual capacity or perceptual quality of stimuli can also be used, for example, for a computer-assisted communication or for training the volitional control of parts of the body.

SUMMARY OF THE INVENTION

The object of the present invention is therefore to provide a device and a simple method which enables a rapid and targeted acquisition by and training of a test subject in the volitional control of particular bodily functions or the volitional movement of parts of the body, supported by stimuli applied to the relevant parts of the body.

The invention also achieves this object in a device of the type described above having the features specified in the characterizing part of the independent apparatus claim.

Essentially, a training and stimulation assembly according to the invention for training the volitional control of a specified part of the body by a test subject comprises:
 an electrode cap, which has a number of electrodes,
 an evaluation unit, in particular a brain-computer interface, which is connected downstream of the electrode cap and which is designed to measure respective voltages present at the electrodes and to provide measurement results as EEG measurement data, wherein the evaluation unit is designed to analyze the EEG measurement data for the presence of a mental activity and to determine a correspondence value which indicates the correspondence of the EEG measurement data with reference values defined by the mental act,
 a control unit, to which the output of the evaluation unit is supplied, and
 at least one stimulation unit, which is connected downstream of the control unit (4), which is designed to stimulate the body of the test subject at a specified point of the body and/or induce it into movement.

It is also provided that the control unit is designed to control the stimulation unit and to apply an indicating stimulus via the stimulation unit to the part of the body of the test subject, in particular before or during a period of time in which the test subject is required to perform mental activities in relation to the part of the body.

An effective means of checking whether or not the training effect can be increased in a test subject by the application of an indicating stimulus is provided by the fact that the evaluation unit is designed to analyze the EEG measurement data of the test subject at a plurality of specified time points within the recording period during and/or after the delivery of the indicating stimulus, for the presence of a mental activity induced by the indicating stimulus or temporally related thereto, and to detect a mental activity thus identified as a response to the indicating stimulus.

To increase the effectiveness of the learning and training of the volitional control of particular bodily functions and/or the deliberate movement of parts of the body, it is provided that the control unit is designed to determine the correspondence value determined by the evaluation unit at a plurality of specified time points within the recording period during and/or after the delivery of the indicating stimulus and, if this correspondence value indicates a mental activity, to place an activation stimulus associated with this activity at the relevant part of the body by means of the stimulation unit.

The fact that instructions for performing mental activities reach the test subjects in a targeted way is ensured by an instruction unit being provided, and by the fact that the control unit is designed to cause the instruction unit to issue instructions to the test subject, in particular an instruction from a predefined number of instructions, wherein in particular the instruction unit comprises a loudspeaker and the control unit is designed to control the instruction unit to issue a voice message which has an acoustic instruction for the test subject to carry out a mental activity in relation to the body part.

An effective training of the volitional control of various bodily functions or the volitional movement of different parts of the body by stimulation of the affected parts of the body of the test subject is achieved by a plurality of stimulation units being provided, wherein each of the stimulation units is assigned to a particular body part and is designed to transmit stimuli to the relevant body part, that the evaluation unit is designed to analyze incoming EEG measurement data for the presence of the different mental activities in the relevant body parts, and that the control unit is designed to select one of the body parts and the stimulus assigned to said body part according to predefined criteria, in particular according to random criteria, and to deliver an associated indicating stimulus, including if appropriate an associated instruction.

An increase in the learning effect during the training of the volitional movement of body parts can be achieved by placing an additional stimulus on the part of the body concerned when, for example, the subject thinks of just this part of the body. The effectiveness of the training of the volitional control of parts of the body is therefore increased by the fact that the control unit is designed, on detecting a specified mental activity, to activate the stimulation unit associated with this mental activity and to apply a confirmation stimulus via the stimulation unit, in particular, on detecting a mental activity differing from the specified mental activity, to suppress the stimulation of the test subject using other stimulation units and/or to apply the stimuli to a part of the body of the test subject with greater intensity, the greater the correspondence value of the detected mental activity with the assigned mental activity in relation to the relevant body part of the test subject.

Since test subjects respond differently to different stimuli, a large selection of possible stimulators is advantageous in order to achieve an optimum learning outcome with regard to the volitional control of parts of the body by the test subject. It is therefore advantageously provided that the simulation unit comprises stimulators of at least one of the following types for stimulating at least one body part of the test subject:

vibro-tactile actuators for arrangement on the body of the test subject, wherein the vibro-tactile actuators are designed to apply vibration to at least one body part of the test subject, auditory actuators, wherein the auditory actuators are designed to produce different tones or sounds in frequencies audible to the human ear, in particular, that the auditory actuators are designed to produce different tones or sounds with a spatial relationship to the body part of the test subject, in relation to which the test subject is required to perform mental activities, and/or with a relationship to the movement of a body part, which the test subject is required to mentally perform;

it is thus possible, for example, that a test subject who is required to think of a specific bodily movement such as walking, has walking sounds played to them by means of the auditory actuators.

stimulation electrodes for the application of functional electrical stimulation to stimulate a point on the body of the test subject, a mechanical orthosis or robot for manipulating a part of the body of the test subject, electro-stimulators for the stimulation of nerves at a point on the body of the test subject by means of electrical stimuli, temperature stimulators for generating a heat and/or cold stimulus at a point of the body of the test subject, pain stimulators for generating pain at a point of the body of the test subject.

A targeted application of stimuli to a fixed point on the body or a body part of the test subject is ensured by the fact that a fixing device for fastening the stimulation unit on the relevant part of the body of the test subject is provided, in particular that the fixing device is designed for attaching the stimulation unit to a hand or an arm or a foot or a leg or the larynx or tongue of the test subject, in particular that the fixing unit is designed as a glove or sock or plaster or cuff.

For the effective learning of the volitional control of a specified body part by the test subject, a method is also provided for training the volitional control of body parts, a) wherein the test subject is tasked with mental activities in relation to a specific body part, which are to be performed when an indicating stimulus is present, b) wherein at least one indicating stimulus is applied to the body part of the test subject, c) wherein the response of the test subject is detected at a plurality of predefined time points within the recording period during and/or after the delivery of the indicating stimulus, by the EEG measurement data induced by the indicating stimulus or temporally related to the indicating stimulus being determined from a specified number of EEG channels and said EEG measurement data being assigned to the respective body part, d) wherein the EEG measurement data are examined for the presence of a mental activity corresponding to the mental activities assigned to the test subject and e) wherein in the presence of such a mental activity an activation stimulus assigned to this activity is applied at the relevant part of the body of the test subject.

An increase in the training effectiveness can be achieved in a test subject by the fact that given the presence of a mental activity which corresponds to the mental activities assigned to the test subject, an activation stimulus assigned to this activity is applied to the body part of the test subject.

To provide a simple means of checking whether or not the training effect can be increased in a test subject by the application of an indicating stimulus, it is provided that the EEG measurement data of the test subject are analyzed at a plurality of specified time points within the recording period during and/or after the delivery of the indicating stimulus, for the presence of a mental activity induced by the indicating stimulus or temporally related thereto, wherein the identified mental activity is detected as a response to the indicating stimulus.

In a method according to the invention, for learning and/or for training the volitional control and/or movement of different parts of the body it is advantageously provided that a plurality of mental activities is defined for the test subject, that one of these mental activities is selected for the test subject and communicated to the test subject and an associated activation stimulus is applied to the test subject, and that a confirmation stimulus is only applied to the test subject if the mental activity of the test subject identified from the EEG measurement data corresponds to the specified mental activity.

In order to make the largest possible selection of different stimuli available to enable an individual effective training of the volitional control of parts of the body for the test subject, it is provided that stimuli of at least one of the following types are applied as an indicating stimulus using stimulators for the stimulation of at least one body part of the test subject:

vibro-tactile stimuli, the vibro-tactile stimuli being applied to the test subject by means of vibro-tactile actuators, auditory stimuli, in particular different tones or sounds in frequencies audible to the human ear, the respective tones or sounds being played to the test subject by means of auditory actuators, functional electro-stimulation, the functional electro-stimulation being applied by means of stimulation electrodes at a point of the test subject's body, manipulation of a body part of the test subject by means of a mechanical orthosis or a robot, electrical stimuli, the electrical stimuli being applied by means of electrical stimulators for the stimulation of nerves at a point of the test subject's body, heat and/or cold stimuli, the heat and/or cold stimuli being applied to the test subject by means of temperature stimulators, pain stimuli, the pain stimuli being applied to the test subject by means of pain stimulators.

To provide simple stimulation of body parts of the test subject it is advantageously provided that the stimulators for generating stimuli are arranged on the body of the test subject, in particular, that the stimulators for generating stimuli are arranged by means of a fixing device on a hand or an arm or a foot or a leg or the larynx or tongue of the test subject, the stimulators being preferably fastened by means of a fixing device designed as a glove or sock or plaster or collar.

It is of particular advantage for the learning behavior of the test subject if an application of functional electrical stimulation is made to a part of the body of the test subject as an activation stimulus, or that a part of the body of the test subject is manipulated or moved with a mechanical orthosis or a robot as the activation stimulus.

The training effect in the subject is advantageously increased by the fact that the stimuli are applied to a body part of the test subject with greater intensity, the better the correspondence of the detected mental activity with the assigned mental activity in relation to the relevant body part of the test subject.

Further advantages and embodiments of the invention are derived from the description and the enclosed drawings.

Particularly advantageous exemplary embodiments of the invention, but not to be understood as being restrictive, are illustrated schematically in the following on the basis of the enclosed drawings and described by reference to the drawings:

DESCRIPTION OF THE INVENTION

Figure 1:
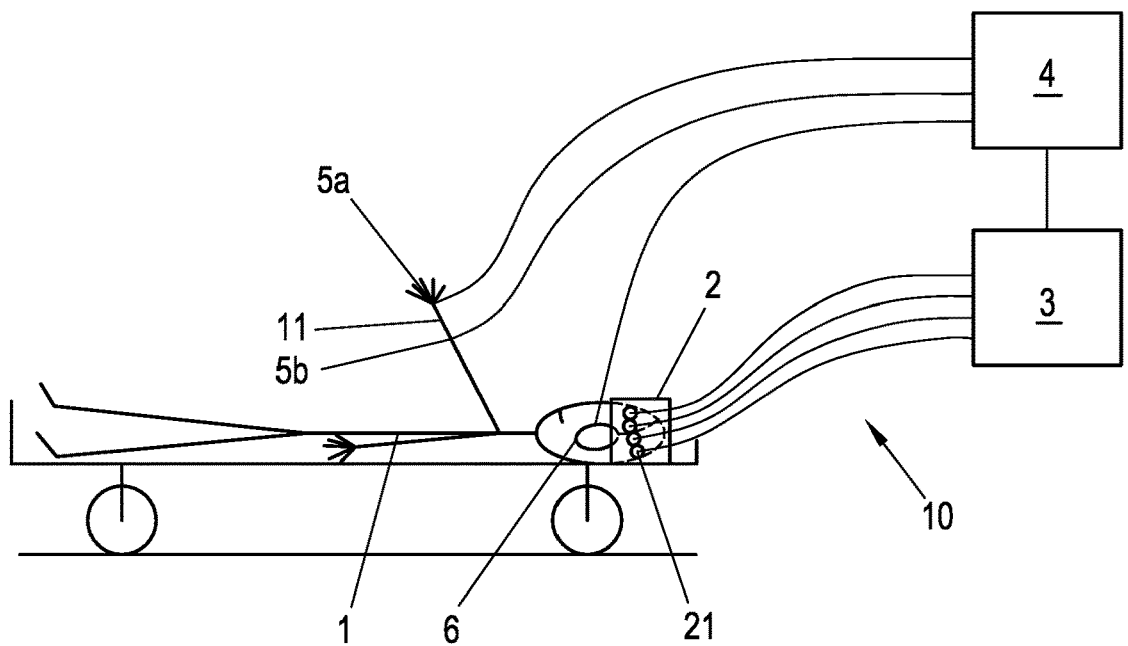
FIG. 1 schematically shows an exemplary embodiment of a training and stimulation assembly for implementing a method according to the invention.

FIG. 1 shows a person lying in a bed, hereafter referred to as the test subject 1, who is to learn to voluntarily control a specified body part 11 using a training and stimulation assembly 10. In the example, the specified body part 11 is the left hand. The test subject 1 wears an electrode cap 2, which in the example has four electrodes 21, each of which is connected to an evaluation unit 3 by means of an EEG cable connection. The output of the evaluation unit is fed to a control unit 4. The control unit 4 is additionally connected to an instruction unit 6, which in the exemplary embodiment is implemented as a set of headphones, which is worn on the head of the test subject 1.

Stimulation units 5a, 5b are connected downstream of the control unit 4, which are designed to stimulate the body of the test subject 1 at a specified point and/or induce it into motion.

The evaluation unit 3 is in particular a brain-computer interface, which is designed to measure the voltages present at the electrodes 21 and to provide the EEG measurement data, which comprise one measuring channel for each electrode 21, to each of which consecutively recorded voltage readings are assigned.

The control unit 3 analyzes the EEG measurement data for the presence of a mental activity and determines a correspondence value, which indicates the correspondence of the EEG measurement data with predetermined reference values, wherein the reference values are defined by the mental activity.

The control unit 4 is designed to control the stimulation units 5a, 5b and to apply an indicating stimulus via the stimulation units 5a, 5b to the body part 11 of the test subject 1 before or during a period of time in which the test subject 1 is required to perform mental activities in relation to the part of the body 11. In addition, the control unit 4 controls the instruction unit 6 to issue a voice message to the test subject 1.

The voice message issued by the instruction unit 6 can contain, for example, an acoustic instruction for the test subject 1 to perform a mental activity in relation to the body part 11. Thus, for example, it may be communicated to the test subject 1 to think of his/her left hand or to mentally execute a movement with the left hand, while an indicating stimulus is applied to the left hand, or else after an indicating stimulus has been applied to the left hand.

The evaluation unit 3 supplies the control unit 4 with the EEG measurement data recorded during a recording period and, in particular, the correspondence values of the EEG measurement data with predetermined reference values. The control unit 4 accesses the correspondence value determined by the evaluation unit 3 at a plurality of specified time points within the recording period during and/or after the delivery of the indicating stimulus and, if this correspondence value indicates a mental activity, controls the stimulation units 5a, 5b to apply an activation stimulus associated with this activity on the relevant body part 11.

In the specific exemplary embodiment an indicating stimulus is applied to the left hand of the test subject 1 while he/she is required to think of his/her left hand. In the event that the evaluation unit 3 determines that the test subject 1 is subsequently actually thinking of his/her left hand during or after the indicating stimulus is applied to it, a positive correspondence value is provided at the output of the evaluation unit 3. Due to the correspondence of the stimulation units 5a, 5b, the control unit 4 causes an activation stimulus to be applied to the left hand of the test subject 1, so that the connection between the volitional control of the left hand and an actual movement of the left hand is reinforced by the stimulation.

Alternatively, a plurality of stimulation units 5a, 5b can also be provided, which are each assigned to different parts of the body and designed to transmit stimuli to the particular body part 11 concerned. In this case the evaluation unit 3 analyzes the incoming EEG measurement data with regard to the presence of different mental activities in relation to the relevant body parts and the control unit 4 issues instructions concerning a selected body part 11 and the stimulus assigned to this body part 11 according to predefined criteria.

In the event that, for example, the specified mental activity involves thinking of the left foot and the test subject 1 is thinking of the left foot, the control unit 4 applies a confirmation stimulus to the left foot of the test subject 1 by means of the associated stimulation unit 5a.

In addition or alternatively, it can also be provided that the better the correspondence of the detected mental activity with the task of thinking about the left foot, the greater the intensity with which the control unit 4 applies stimuli to the left foot of the subject 1 using the associated stimulation unit 5a.

If the detected mental activity does not correspond to the specified thinking about the left foot and, for example, the test subject 1 is thinking of the right foot, the control unit 4 can also be designed to suppress the stimulation of the test subject 1 by other stimulation units 5b, for example those located on the right foot.

The invention can also be used to train the ability of a test subject 1 to distinguish between their right and left limbs, for example, the left and the right hand. In this case, for example, a stimulation unit 5a is arranged on the left hand of the subject 1 and an indicating stimulus is applied to the left hand of the subject 1 while he/she is required to think about their left hand or execute a mental movement with their left hand. The instruction to think about the left hand while at the same time issuing the indicating stimulus to the left hand is issued repeatedly until a specified number of repetitions is reached in a specified period of time.

Test subjects 1 who have difficulties in distinguishing between their right and left hand find it difficult at the beginning of the training to actually think about the left hand when the instruction is issued, and the test subject 1 instead thinks about the right hand. Since an indicating stimulus is applied only to the left hand, the association between the volitional control of the left hand and an actual movement of the left hand is reinforced. This means that with an increasing number of repetitions the test subject 1 finds it easier to make the distinction between the right and the left hand.

Depending on the individual's ability to perceive different stimuli and the perception intensity of the stimuli for the test subject 1, different kinds of stimuli can be chosen as the indicating, activation, or confirming stimulus, which can be applied to the test subject 1 by means of stimulators of the stimulation units 5a, 5b. Possible types of stimuli include, for example, vibration application, temperature stimulation, pain stimulation, electrical stimulation or functional electrical stimulation of at least one body part 11 of the test subject 1, or a movement or manipulation of the body part 11 by means of a mechanical orthosis or a robot.

Also suitable as stimuli are different tones or sounds in frequencies audible for a human being that have a spatial relationship to the relevant body part 11, in relation to which the test subject 1 is required to perform mental activities, or else different tones or sounds relating to the movement with a body part 11, which the test subject 1 is required to mentally perform, such as the sound of footsteps.

The control unit 3 is furthermore designed to evaluate the EEG measurement data recorded during a recording period during and/or after the issue of the indicating stimulus as to whether a mental activity induced by the indicating stimulus or temporally related thereto is present, in order thus to determine whether the test subject 1 responds to the application of an indicating stimulus.

In this way it can be determined whether for training a volitional control of the left hand in a test subject 1, for example, the arrangement of vibro-tactile stimulators on the fingers of the left hand or of stimulators for functional electrical stimulation of the left forearm of the test subject 1 will be effective.

The evaluation unit 3 may determine in a test subject 1, for example, no response to the application of an indicating stimulus via the vibro-tactile stimulators on the fingers of the left hand, whereas the test subject 1 responds to the application of an indicating stimulus via the stimulators for functional electrical stimulation on the left forearm. In this case, the effectiveness of the training can be increased by only applying the indicating stimulus in test subject 1 via the stimulators for functional electrical stimulation on the left forearm.

Figure 2:
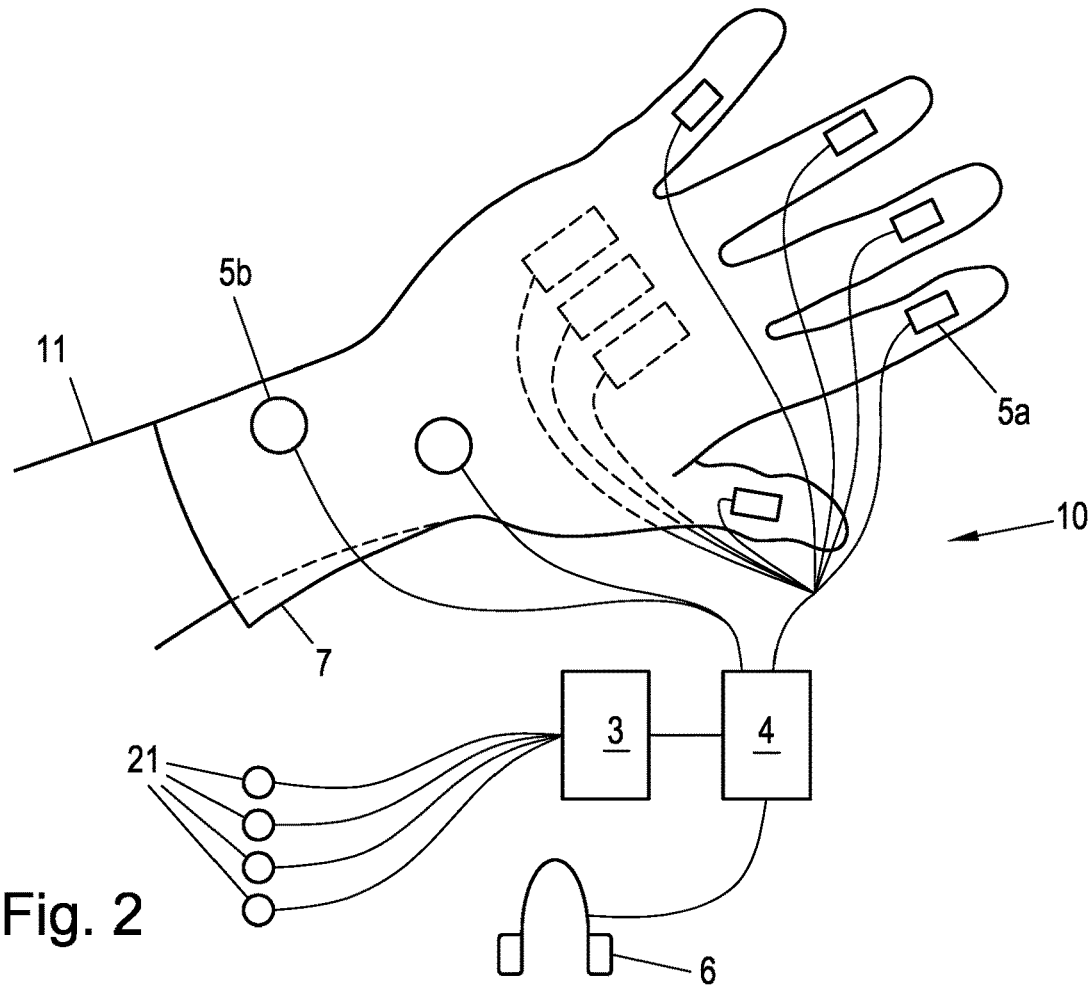
FIG. 2 shows a detail of the assembly shown in FIG. 1.

FIG. 2 shows a schematic view of a detail from FIG. 1, which illustrates in detail the exemplary embodiment shown in FIG. 1 of a training and stimulation assembly 10. The training and stimulation assembly 10 in the exemplary embodiment comprises, as described above, electrodes 21 of an electrode cap 2 which are connected to an evaluation unit 3, a control unit 4 which is connected downstream of the control unit 3 and is connected to an instruction unit 6 and stimulation units 5a, 5b downstream of the control unit 4.

On the body part 11 of the test subject 1, for which he/she is required to learn the volitional control—in the example it is the left hand—a fixing device 7 is located for attaching the stimulation units 5a, 5b to the left hand. The fixing device 7 in the example is implemented as a glove.

The stimulation units 5a, 5b in this exemplary embodiment comprise a vibro-tactile stimulation unit 5a and a stimulation unit 5b for applying functional electrical stimulation. The stimulation unit 5a has five vibro-tactile actuators, which are mounted on the fixing device 7 in such a way that they can apply vibration to the upper side of the fingers of the left hand, while three more vibro-tactile actuators are mounted on the fixing device 7 such that they can be used to apply vibration to the palm of the left hand. The stimulation unit 5b for the application of functional electrical stimulation has two stimulation electrodes, which are designed to apply functional electrical stimulation to stimulate the forearm of the left hand, and is arranged on the left hand of the test subject 1 in the area of the wrist.

In the execution of a method in accordance with the embodiment of the invention, a method according to the invention for training the volitional control of the left hand, the test subject 1 is required to perform mental activities in relation to the left hand, for example, a mental execution of a movement with the left hand, which are to be executed when an indicating stimulus is present, wherein at least one indicating stimulus is applied to the left hand of the test subject 1. In the embodiment of the training and stimulation assembly 10 shown in FIG. 2, a vibration applied, for example, to the fingers or the palm of the left hand is used as the indicating stimulus.

The response of the test subject 1 is detected at a plurality of predefined time points within the recording period during and/or after the vibration stimulus is applied to the left hand. For this purpose, the EEG measurement data induced by the indicating stimulus or temporally related to the indicating stimulus are determined by means of the electrodes 21 and in the example, assigned to the left hand.

The EEG measurement data are examined for the presence of the mental execution of a movement with the left hand, which the subject 1 was required to perform in relation to the left hand. If a mental execution of a movement with the left hand is present, an activation stimulus associated with this activity is applied to the left hand of the test subject 1. In the design variant of the training and stimulation assembly 10 shown, the activation stimulus is applied as a functional electrical stimulation of the left forearm.

Alternatively, it can be provided that the application of the activation stimulus, thus for example the application of the functional electrical stimulation of the left forearm of the test subject 1, is carried out with greater intensity the better the correspondence of the detected mental activity with the instructed mental execution of a movement with the left hand in the test subject 1.

In addition, for training the volitional control of different parts of the body or different bodily functions, the fixing device 7 for attaching the stimulation units 5a, 5b is implemented, for example, as a sock for training the volitional movement of a foot or a leg, or for the training of swallowing as a plaster to be attached to the tongue or as a collar for attaching to the larynx of the test subject 1.

In order to train the volitional control of different parts of the body or of different bodily functions, it can also be provided that a plurality of different mental activities is specified for the test subject 1 in relation to various parts of the body. Thus, in one embodiment of the invention for training the mental control of both hands and feet in a test subject 1, for example, a total of four stimulation units are placed on the test subject 1, wherein one stimulation unit 1 is attached to each of the right hand, the left hand, the right foot and the left foot. In the control unit 4 in this case there are four different instructions relating to one of the four parts of the body.

The control unit 4 is designed to select one of the body parts in each case and the stimulus associated with this body part according to predefined criteria, in particular, random criteria. The control unit 4 applies an indicating stimulus to the test subject 1 with regard to the selected body part and issues an associated instruction for the test subject 1 by means of an instruction unit 6.

The control unit 3 analyzes the incoming EEG measurement data for the presence of the different mental activities in the relevant parts of the body, and if a correspondence is detected between the mental activity and the instructed activity, a confirmation stimulus is applied to the test subject 1 by the control unit 4 by means of the stimulation unit located on the corresponding part of the body.

This means that if the right hand is selected by the control unit 4, an indicating stimulus is applied to the right hand of the test subject 1 and the subject 1 is instructed, for example, to think about the right hand. If the test subject 1 is actually thinking about their right hand, a correspondence between the executed and instructed mental activities is detected and the control unit 4 applies a confirmation stimulus to the right hand of the test subject 1.

In the event that no correspondence of the mental activity with the instructed activity is detected, the control unit 4 suppresses the stimulation of the test subject 1 by other stimulation units. This means that if the test subject 1 is thinking, for example, about the right foot instead of the right hand, no confirmation stimulus is applied to the right foot, but that in this case the confirmation stimulus is not applied.

The invention claimed is:

1. A training and stimulation assembly for training a volitional control of a specified body part by a test subject, the training and stimulation assembly comprising:
    an electrode cap having a number of electrodes;
    an evaluation unit connected downstream of said electrode cap and configured to measure respective voltages present at said electrodes and to provide measurement results as electroencephalography (EEG) measurement data, said evaluation unit being configured to analyze the EEG measurement data for a presence of mental activity and to determine a correspondence value which indicates a correspondence of the EEG measurement data with reference values defined by a mental act, said evaluation unit configured to analyze the EEG measurement data for a presence of different mental activities in relevant body parts;
    a controller receiving an output of said evaluation unit, said controller configured to select any one of the relevant body parts and a stimulus being assigned to said one relevant body part according to predefined criteria, and to deliver an associated indicating stimulus, including an associated instruction;
    at least one stimulator connected downstream of said controller, said at least one stimulator being configured to stimulate a body of the test subject at a specified point of the body and/or induce the body into motion, said at least one stimulator being one of a plurality of stimulators, each of said stimulators being assigned to a particular body part and configured to transmit stimuli to the particular body part;
    said controller being configured to control said at least one stimulator and to apply an indicating stimulus via said at least one stimulator to the specified body part of the test subject; and
    said controller being configured, on detecting a specified mental activity, to activate said at least one stimulator associated with the specified mental activity and to apply a confirmation stimulus via said at least one stimulator, said controller:
        on detecting the mental activity differing from the specified mental activity, to suppress a stimulation of the test subject using another one of said stimulators; and/or
        applying a stimuli to the specified body part of the test subject with greater intensity, a greater the correspondence value of detected mental activity with instructed mental activity in relation to the specified body part of the test subject.

2. The training and stimulation assembly according to claim 1, wherein said evaluation unit is configured to analyze the EEG measurement data of the test subject at a plurality of specified time points within a recording period during and/or after a delivery of the indicating stimulus, for a presence of mental activity induced by the indicating stimulus or temporally related thereto, and to detect the mental activity thus identified as a response to the indicating stimulus.

3. The training and stimulation assembly according to claim 2, wherein said controller is configured to determine the correspondence value determined by said evaluation unit at the plurality of specified time points within the recording period during and/or after the delivery of the indicating stimulus and, if the correspondence value indicates the mental activity, to apply an activation stimulus associated with the mental activity to a relevant part of the body by means of said at least one stimulator.

4. The training and stimulation assembly according to claim 1, further comprising an instruction unit, said controller being configured to cause said instruction unit to issue instructions to the test subject.

5. The training and stimulation assembly according to claim 1, wherein said at least one stimulator configured to stimulate at least one body part of the test subject, said at least one stimulator selected from the group consisting of:
    vibro-tactile actuators for arrangement on the body of the test subject, wherein said vibro-tactile actuators are configured to apply vibration to the specified body part of the test subject;
    an auditory actuator configured to produce different tones or sounds in frequencies audible to a human ear in relation to which the test subject is required to perform mental activities, and/or with a relationship to a movement of the specified body part, which the test subject is required to mentally perform;
    stimulation electrodes for an application of functional electrical stimulation to stimulate the specified body part of the test subject;
    a mechanical orthosis or robot for manipulating the specified body part of the test subject;
    electro-stimulators for a stimulation of nerves at the specified point on the specified body part of the test subject by means of electrical stimuli;
    temperature stimulators for generating a heat and/or cold stimulus at a point of the specified body part of the test subject; and
    pain stimulators for generating pain at a point of the specified body part of the test subject.

6. The training and stimulation assembly according to claim 1, further comprising a fixing device for fastening said at least one stimulator to the specified body part of the test subject.

7. A method for training a volitional control of body parts in a test subject, which comprises the steps of:
  assigning to the test subject mental activities in relation to a specific body part, which are to be performed when an indicating stimulus is present;
  applying the indicating stimulus to the specific body part of the test subject;
  detecting a response of the test subject at a plurality of predefined time points within a recording period during and/or after a delivery of the indicating stimulus, by electroencephalography (EEG) measurement data from a specified number of EEG channels, induced by the indicating stimulus or temporally related to the indicating stimulus, being determined and the EEG measurement data being assigned to the specific body part;
  examining the EEG measurement data for a presence of mental activity corresponding to the mental activities assigned to the test subject; and
  applying stimuli to the specific body part of the test subject with greater intensity and a better correspondence of detected mental activity to the assigned mental activity in relation to the specific body part of the test subject.

8. The method according to claim 7, wherein when a presence of the mental activity which corresponds to the mental activities assigned to the test subject, applying an activation stimulus assigned to the mental activity to the specific body part of the test subject.

9. The method according to claim 7, which further comprises analyzing the EEG measurement data of the test subject at a plurality of specified time points within the recording period during and/or after the delivery of the indicating stimulus, for the presence of mental activity induced by the indicating stimulus or temporally related thereto, wherein an identified mental activity is detected as a response to the indicating stimulus.

10. The method according to claim 7, which further comprises:
  specifying a plurality of the mental activities for the test subject;
  selecting one of the mental activities for the test subject and communicating, to the test subject, an associated activation stimulus being applied to the test subject; and
  applying a confirmation stimulus only to the test subject when a mental activity of the test subject identified from the EEG measurement data corresponds to a specified mental activity.

11. The method according to claim 7, which further comprises applying stimuli of at least one of the following types as the indicating stimulus using stimulators for stimulation of the specific body part of the test subject:
  vibro-tactile stimuli, the vibro-tactile stimuli being applied to the test subject by means of vibro-tactile actuators;
  auditory stimuli, including different tones or sounds in frequencies audible to a human ear, the different tones or sounds being played to the test subject by means of auditory actuators;
  functional electro-stimulation, the functional electro-stimulation being applied by means of stimulation electrodes at a point of the specific body part of the test subject;
  manipulation of the specific body part of the test subject by means of a mechanical orthosis or robot;
  electrical stimuli, the electrical stimuli being applied by means of electrical stimulators for stimulation of nerves at a point of the specific body part of the test subject;
  heat and/or cold stimuli, the heat and/or cold stimuli being applied to the test subject by means of temperature stimulators; and
  pain stimuli, the pain stimuli being applied to the test subject by means of pain stimulators.

12. The method according to claim 11, which further comprises disposing the stimulators for generating stimuli on the specific body part of the test subject.

13. The method according to claimed in claim 7, which comprises performing one of:
  making an application of functional electrical stimulation to the specific body part of the test subject as an activation stimulus; or
  manipulating or moving the specific body part of the test subject with a mechanical orthosis or a robot as an activation stimulus.

* * * * *